United States Patent [19]

Cleary et al.

[11] Patent Number: 4,495,106
[45] Date of Patent: Jan. 22, 1985

[54] ADSORBENT AND PROCESS FOR SEPARATING FATTY ACIDS FROM ROSIN ACIDS

[75] Inventors: Michael T. Cleary, Elmhurst, Ill.; William C. Laughlin, Edmond, Okla.

[73] Assignee: UOP Inc., Des Plaines, Ill.

[21] Appl. No.: 408,100

[22] Filed: Aug. 13, 1982

[51] Int. Cl.$^3$ .............................................. C11C 1/08
[52] U.S. Cl. .................... 260/419; 260/97.6; 260/97.7; 260/420; 260/428; 260/428.5; 260/412.8
[58] Field of Search ............... 260/428, 428.5, 419, 260/412.8, 97.6, 97.7, 420

[56] References Cited

U.S. PATENT DOCUMENTS

| | | | |
|---|---|---|---|
| 2,744,125 | 5/1956 | Meeks et al. | 260/413 |
| 2,985,589 | 5/1961 | Broughton et al. | 210/34 |
| 3,114,782 | 12/1963 | Fleck et al. | 260/674 |
| 3,201,491 | 8/1965 | Stine et al. | 260/676 |
| 3,265,750 | 8/1966 | Peck et al. | 260/666 |
| 3,510,423 | 5/1970 | Neuzil et al. | 208/310 |
| 3,558,730 | 1/1971 | Neuzil | 260/674 |
| 3,558,732 | 1/1971 | Neuzil | 260/674 |
| 3,626,020 | 12/1971 | Neuzil | 260/674 SA |
| 3,663,638 | 5/1972 | Neuzil | 260/674 SA |
| 3,668,267 | 6/1972 | Hedge | 260/674 SA |
| 3,734,974 | 5/1973 | Neuzil | 260/674 SA |
| 3,864,416 | 2/1975 | Campbell et al. | 260/674 A |
| 3,950,365 | 4/1976 | Singer et al. | 260/419 |
| 3,954,819 | 5/1976 | Husch | 260/428 |
| 3,976,671 | 8/1976 | Husch | 260/428 |
| 4,048,205 | 9/1977 | Neuzil et al. | 260/428 |
| 4,061,724 | 12/1977 | Grose et al. | 423/335 |
| 4,104,294 | 8/1978 | Grose et al. | 260/448 C |
| 4,329,280 | 5/1982 | Cleary et al. | 260/97.6 |
| 4,404,145 | 9/1983 | Cleary et al. | 260/419 |

OTHER PUBLICATIONS

Flanigen et al., Nature, vol. 271, No. 5645, pp. 512–516, (1978).

Primary Examiner—Helen M. S. Sneed
Attorney, Agent, or Firm—James R. Hoatson, Jr.; Louis A. Morris; William H. Page, II

[57] ABSTRACT

This invention comprises a process for separating a fatty acid from a mixture comprising a fatty acid and a rosin acid, which process comprises contacting the mixture at separation conditions with a molecular sieve comprising silicalite in a silica matrix the precursor of the molecular sieve comprising silicalite powder dispersed in colloidal amorphous silica, the precursor having been gelled and then treated in a manner to substantially eliminate hydroxyl groups from the molecular sieve, thereby selectively retaining the fatty acid. The fatty acid is recovered from the molecular sieve by displacement with a displacement material comprising an organic acid.

21 Claims, 1 Drawing Figure

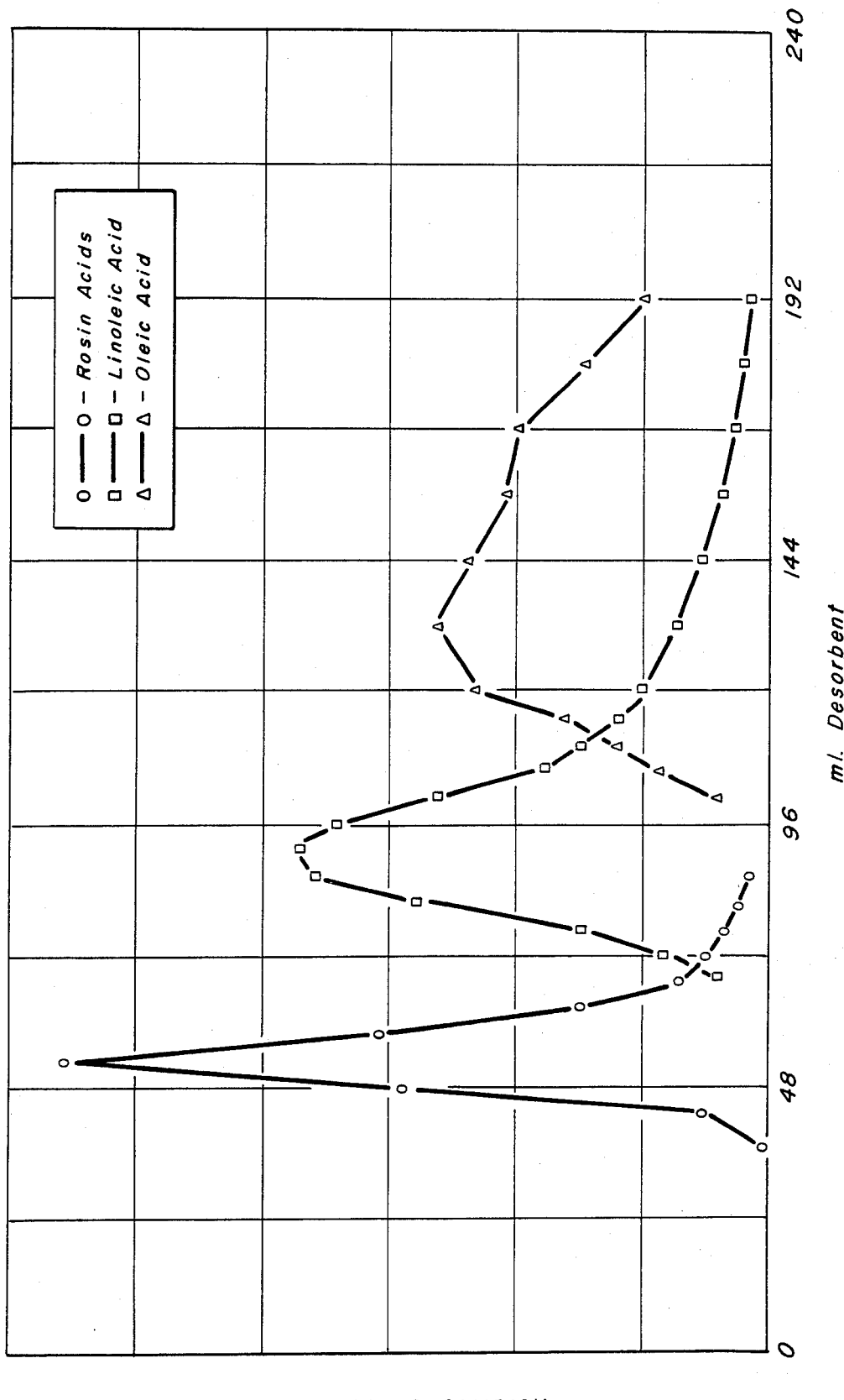

ADSORBENT AND PROCESS FOR SEPARATING FATTY ACIDS FROM ROSIN ACIDS

BACKGROUND OF THE INVENTION

1. Field of the Invention

The field of art to which this invention pertains is the solid bed molecular sieve separation of fatty acids. More specifically, the invention relates to a process for separating a fatty acid from a rosin acid which process employs a molecular sieve comprising silicalite in a silica matrix.

2. Description of the Prior Art

It is well known in the separation art that certain crystalline aluminosilicates can be used to separate hydrocarbon types from mixtures thereof. As a few examples, a separation process disclosed in U.S. Pat. Nos. 2,985,589 and 3,201,491 uses a type A zeolite to separate normal paraffins from branched chain paraffins, and processes described in U.S. Pat. Nos. 3,265,750 and 3,510,423 use type X or type Y zeolites to separate olefinic hydrocarbons from paraffinic hydrocarbons. In addition to their use in processes for separating hydrocarbon types, X and Y zeolites have been employed in processes to separate individual hydrocarbon isomers. As a few examples, absorbents comprising X and Y zeolites are used in the process described in U.S. Pat. No. 3,114,782 to separate alkyl-trisubstituted benzene isomers; in the process described in U.S. Pat. No. 3,864,416 to separate alkyltetrasubstituted monocyclic aromatic isomers; and in the process described in U.S. Pat. No. 3,668,267 to separate specific alkylsubstituted naphthalenes. Because of the commercial importance of para-xylene, perhaps the more well-known and extensively used hydrocarbon isomer separation processes are those for separating para-xylene from a mixture of $C_8$ aromatics. In processes described in U.S. Pat. Nos. 3,558,730; 3,558,732; 3,626,020; 3,663,638; and 3,734,974, for example, molecular sieves comprising particular zeolites are used to separate para-xylene from feed mixtures comprising para-xylene and at least one other xylene isomer by selectively adsorbing para-xylene over the other xylene isomers.

In contrast, this invention relates to the separation of non-hydrocarbons and more specifically to the separation of fatty acids. Substantial uses of fatty acids are in the plasticizer and surface active agent fields. Derivatives of fatty acids are of value in compounding lubricating oil, as a lubricant for the textile and molding trade, in special lacquers, as a water-proofing agent, in the cosmetic and pharmaceutical fields, and in biodegradable detergents.

It is known from U.S. Pat. No. 4,048,205 to use type X and type Y zeolites for the separation of unsaturated from saturated esters of fatty acids. The type X and type Y zeolites, however, will not separate the esters of rosin acids found in tall oil from the esters of fatty acids nor the free acids, apparently because the pore size of those zeolites (over 7 angstroms) are large enough to accommodate and retain the relatively large diameter molecules of esters of rosin acids as well as the smaller diameter molecules of esters of fatty acids (as well as the respective free acids). Type A zeolite, on the other hand, has a pore size (about 5 angstroms) which is unable to accommodate either of the above type esters (or free acids) and is, therefore, unable to separate them. An additional problem when a zeolite is used to separate free acids is the reactivity between the zeolite and free acids.

It is also known that silicalite, a non-zeolite hydrophobic crystalline silica molecular sieve, exhibits molecular sieve selectivity for a fatty acid with respect to a rosin acid, particularly when used with a specific displacement fluid. Silicalite, however, a fine powder, must be bound in some manner to enable its practical use as a molecular sieve. All binders heretofore attempted are not suitable for use in separating the components of tall oil because of the binder's reactivity or interference with the separation. We have discovered a binder which when incorporated with the silicalite provides a new molecular sieve uniquely suitable for the separation of the components of tall oil.

SUMMARY OF THE INVENTION

In brief summary, the invention is, in one embodiment, a molecular sieve comprising silicalite in a silica matrix. The precursor of the molecular sieve comprises silicalite powder dispersed in colloidal amorphous silica. The precursor is gelled and then treated in a manner effecting substantially complete elimination of hydroxyl groups on the molecular sieve.

In another embodiment, our invention is a process for separating a fatty acid from a mixture comprising a fatty acid and a rosin acid. The process comprises contacting the mixture at separation conditions with a molecular sieve comprising silicalite in a silica matrix. The precursor of the molecular sieve comprises silicalite powder dispersed in collodial amorphous silica. The precursor is gelled and then treated in a manner effecting substantially complete elimination of hydroxyl groups on the molecular sieve, thereby selectively retaining the fatty acid thereon. The rosin acid is removed from the fatty acid containing molecular sieve.

In still another embodiment, our invention is a process for separating a fatty acid from a mixture comprising fatty acid and a rosin acid. The process employs a molecular sieve comprising silicalite in a silica matrix. The precursor of the molecular sieve comprises silicalite powder dispersed in collodial amorphous silica, the precursor having been gelled and then treated in a manner effecting substantially complete elimination of hydroxyl groups on the molecular sieve. The process comprises the steps of: (a) maintaining net liquid flow through a column of the molecular sieve in a single direction, which column contains at least three zones having separate operational functions occurring therein and being serially interconnected with the terminal zones of the column connected to provide a continuous connection of the zones; (b) maintaining a retention zone in the column, the zone defined by the molecular sieve located between a feed inlet stream at an upstream boundary of the zone and a raffinate outlet stream at a downstream boundary of the zone; (c) maintaining a purification zone immediately upstream from the retention zone, the purification zone defined by the molecular sieve located between an extract outlet stream at an upstream boundary of the purification zone and the feed inlet stream at a downstream boundary of the purification zone; (d) maintaining a displacement zone immediately upstream from the purification zone, the displacement zone defined by the molecular sieve located between a displacement fluid inlet stream at an upstream boundary of the zone and the extract outlet stream at the downstream boundary of the zone; (e) passing the feed stream into the retention zone at separation conditions to effect the selective retention of fatty acid by the molecular sieve in the retention zone and withdrawing a raffinate outlet stream from the retention zone; (f) passing a displacement fluid into said displacement zone at displacement conditions to effect the displacement of the fatty acid from the adsorbent in the displacement zone; (g) withdrawing an extract stream comprising the fatty acid and displacement fluid from the displacement zone; and (h) periodically advancing through the column of molecular sieve in a downstream direction with respect to fluid flow in the retention zone, the feed inlet stream, raffinate outlet stream, displacement fluid inlet stream, and extract outlet and raffinate outlet streams.

In yet another embodiment, our invention is a method of manufacturing a molecular sieve comprising silicalite in a silica matrix, which method comprises: (a) mixing silicalite powder into an aqueous colloidal dispersion of amorphous particles; (b) gelling the mixture; and (c) treating the gelled mixture in a manner effecting complete substantially elimination of hydroxyl groups on the molecular sieve.

Other embodiments of our invention encompass details about feed mixtures, molecular sieves, displacement fluids and operating conditions, all of which are hereinafter disclosed in the following discussion of each of the facets of the present invention.

DESCRIPTION OF THE INVENTION

At the outset the definitions of various terms used throughout the specification will be useful in making clear the operation, objects and advantages of this process.

A "feed mixture" is a mixture containing one or more extract components and one or more raffinate components to be separated by this process. The term "feed stream" indicates a stream of a feed mixture which passes to the molecular sieve used in the process.

An "extract component" is a compound or type of compound that is retained by the molecular sieve while a "raffinate component" is a compound or type of compound that is not retained. In this process a fatty acid is an extract component and a rosin acid is a raffinate component. The term "displacement fluid" shall mean generally a fluid capable of displacing an extract component. The term "displacement fluid stream" or "displacement fluid input stream" indicates the stream through which displacement fluid material passes to the molecular sieve. The term "raffinate stream" or "raffinate output stream" means a stream through which a raffinate component is removed from the molecular sieve. The composition of the raffinate stream can vary from essentially a 100% displacement fluid to essentially 100% raffinate components. The term "extract stream" or "extract output stream" shall mean a stream through which an extract material which has been displaced by a displacement fluid is removed from the molecular sieve. The composition of the extract stream, likewise, can vary from essentially 100% displacement fluid to essentially 100% extract components. At least a portion of the extract stream and preferably at least a portion of the raffinate stream from the separation process are passed to separation means, typically fractionators, where at least a portion of displacement fluid and diluent is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity, fatty acid product or a rosin acid product (or both) at high recoveries, it will be appreciated that an extract component is never completely retained by the molecular sieve, nor is a raffinate component completely not retained by the molecular sieve. Therefore, varying amounts of a raffinate component can appear in the extract stream and, likewise, varying amounts of an extract component can appear in the raffinate stream. The extract and raffinate streams then are further distinguished from each other and from the feed mixtures by the ratio of the concentrations of an extract component and a raffinate component appearing in the particular stream. More specifically, the ratio of the concentration of a fatty acid to that of non-retained rosin acid will be lowest in the raffinate stream, next highest in the feed mixture, and the highest in the extract stream. Likewise, the ratio of the concentration of a rosin acid to that of the fatty acid will be highest in the raffinate stream, next highest in the feed mixture, and the lowest in the extract stream.

The term "selective pore volume" of the molecular sieve is defined as the volume of the molecular sieve which selectively retains an extract component from the feed mixture. The term "non-selective void volume" of the molecular sieve is the volume of the molecular sieve which does not selectively retain an extract component from the feed mixture. This latter volume includes the cavities of the molecular sieve which admit raffinate components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

When molecular sieve "passes" into an operational zone (hereinafter defined and described) employed in one embodiment of this process, its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is a net entrainment of liquid into the zone by the molecular sieve. Since this net entrainment is a fluid present in non-selective void volume of the molecular sieve, it in most instances comprises non-retained feed components. The selective pore volume of a molecular sieve can in certain instances adsorb portions of raffinate material from the fluid surrounding the molecular sieve since in certain instances there is competition between extract material and raffinate material for adsorptive sites within the selective pore volume. If a large quantity of raffinate material with respect to extract material surrounds the molecular sieve, raffinate material can be competitive enough to be retained by the molecular sieve.

Before considering feed mixtures which can be charged to the process of this invention, brief reference is first made to the terminology. The fatty acids are a large group of aliphatic monocarboxylic acids, many of which occur as glycerides (esters of glycerol) in natural fats and oils. Although the term "fatty acids" has been restricted by some to the saturated acids of the acetic acid series, both normal and branched chain, it is now generally used, and is so used herein, to include also related unsaturated acids, certain substituted acids, and even aliphatic acids containing alicyclic substituents. The naturally occurring fatty acids with a few exceptions are higher straight chain unsubstituted acids containing an even number of carbon atoms. The unsaturated fatty acids can be divided, on the basis of the number of double bonds in the hydrocarbon chain, into monoethanoid, diethanoid, triethanoid, etc. (or monoethylenic, etc.). Thus the term "unsaturated fatty acid" is a generic term for a fatty acid having at least one double bond, and the term "polyethanoid fatty acid" means a fatty acid having more than one double bond per molecule. Fatty acids are typically prepared from glyceride fats or oils by one of several "splitting" or hydrolytic processes. In all cases, the hydrolysis reaction may be summarized as the reaction of a fat or oil with water to yield fatty acids plus glycerol. In modern fatty acid plants, this process is carried out by continuous high pressure, high temperature hydrolysis of the fat. Starting materials commonly used for the production of fatty acids include coconut oil, palm oil, inedible animal fats, and the commonly used vegetable oils, soybean oil, cottonseed oil and corn oil.

The source of fatty acids with which the present invention is primarily concerned is tall oil, a by-product of the wood pulp industry, usually recovered from pine wood "black liquor" of the sulfate or Kraft paper process. Tall oil contains about 50–60% fatty acids and about 34–40% rosin acids. The fatty acids include oleic, linoleic, palmitic and stearic acids. Rosin acids, such as abietic acid, are monocarboxylic acids having a molecular structure comprising carbon, hydrogen and oxygen with three fused six-membered carbon rings, which accounts for the much larger molecular diameter of rosin acids as compared to fatty acids. Feed mixtures which can be charged to this process may contain, in addition to esters of the components of tall oil, a diluent material that is not retained by the molecular sieve and which is preferably separable from the extract and raffinate output streams by fractional distillation. When a diluent is employed, the concentration of diluent in the mixture of diluent and acids will preferably be from a few vol.% up to about 75 vol.% with the remainder being fatty acids and rosin acids. Although it has been previously discovered that silicalite is effective for separating esters of fatty and rosin acids, separation of the free acids using silicalite has not heretofore been accomplished.

Displacement fluids used in various prior art adsorptive and molecular sieve separation processes vary depending upon such factors as the type of operation employed. In separation processes which are generally operated continuously at substantially constant pressures and temperatures to ensure liquid phase, and which employ a molecular sieve, the displacement material must be judiciously selected to satisfy many criteria. First, the displacement material should displace an extract component from the molecular sieve with reasonable mass flow rates but yet allow access of an extract component into the molecular sieve so as not to unduly prevent an extract component from displacing the displacement material in a following separation cycle. Displacement fluids should additionally be substances which are easily separable from the feed mixture that is passed into the process. Both the raffinate stream and the extract stream are removed from the molecular sieve in admixture with displacement fluid and without a method of separating at least a portion of the displacement fluid, the purity of the extract product and the raffinate product would not be very high nor would the displacement fluid be available for reuse in the process. It is therefore contemplated that any displacement fluid material used in this process will preferably have a substantially different average boiling point than that of the feed mixture to allow separation of at least a portion of displacement fluid from feed components in the extract and raffinate streams by simple fractional distillation, thereby permitting reuse of displacement fluid in the process. The term "substantially different" as used herein shall mean that the difference between the average boiling points between the displacement fluid and the feed mixture shall be at least about 5° C. The boiling range of the displacement fluid may be higher or lower than that of the feed mixture. Finally, displacement fluids should also be materials which are readily available and therefore reasonable in cost. In the preferred isothermal, isobaric, liquid-phase operation of the process of our invention, we have found displacement fluids comprising organic acids to be effective with short chain organic acids having from 2 to 5 carbon atoms preferred, particularly when, as discussed hereinafter, a diluent is used.

It has been observed that even silicalite may be ineffective in separating fatty and rosin acids upon reuse of the molecular sieve bed for separation following the displacement step. When displacement fluid is present in the bed, selective retention of the fatty acid may not occur. It is hypothesized that the displacement fluid, particularly an organic acid which is the most effective displacement fluid, takes part in or even catalyzes hydrogen-bonded dimerization reactions in which there is an alignment between the molecules of the fatty and rosin acids and, perhaps, the molecules of the displacement fluid. These dimerization reactions may be represented by the formulas:

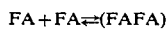

FA+FA⇌(FAFA)

RA+RA⇌(RARA)

FA+RA⇌(FARA)

where FA and RA stand for fatty acids and rosin acids, respectively. The organic acid displacement fluid molecules should probably also be considered reactants and product constituents in the above equations. The dimers would preclude separation of the fatty and rosin acids by blocking access of the former into the pores of the molecular sieve. This hindrance to separation caused by the presence of dimers does not appear to be a significant problem in the aforementioned process for separation of esters of fatty and rosin acids.

It has been discovered that the above dimerization reactions may be minimized, at least to the extent required to enable separation of the rosin and fatty acids, by first flushing the molecular sieve with a suitable diluent. The diluent serves to remove displacement fluid at least from the non-selective void volume of the molecular sieves. Proper selection first requires solubility of the feed stream components in the diluent as well as easy separation of the diluent by conventional means, as with the displacement fluid.

It has also been discovered that even the above pre-flush may be unnecessary if the displacement fluid comprises the organic acid in solution with a properly selected diluent. There are diluents which exhibit the property of minimizing dimerization. The measure of this property was found to be the polarity index of the liquid. Polarity index is as described in the article, "Classification of the Solvent Properties of Common Liquids"; Snyder, L., J. *Chromatography*, 92, 223 (1974), incorporated herein by reference. The minimum polarity index of the displacement fluid diluent required for the process of the present invention, if pre-flush is to be avoided, is 3.5, particularly when the displacement fluid is a short chain organic acid as discussed above. The diluent should comprise from about 50 to about 95 liquid volume percent of the displacement fluid. Polarity indexes for certain selected solvents are as follows:

| SOLVENT | POLARITY INDEX |
| --- | --- |
| Isooctane | −0.4 |
| n-Hexane | 0.0 |
| Toluene | 2.3 |
| p-Xylene | 2.4 |
| Benzene | 3.0 |
| Methylethylketone | 4.5 |
| Acetone | 5.4 |

The molecular sieve to be used in the process of this invention comprises silicalite. As previously mentioned, silicalite is a hydrophobic crystalline silica molecular sieve. Silicalite is disclosed and claimed in U.S. Pat. Nos. 4,061,724 and 4,104,294 to Grose et al, incorporated herein by reference. The silicalite is in a silica matrix the precursor of the molecular sieve comprising silicalite powder dispersed in colloidal amorphous silica, the precursor having been gelled and then treated a manner effecting substantially complete elimination of hydroxyl groups on the molecular sieve. As previously mentioned, silicalite is a hydrophobic crystalline silica molecular sieve. Due to its aluminum-free structure, silicalite does not show ion-exchange behavior, and is hydrophobic and organophilic. Silicalite thus comprises a molecular sieve, but not a zeolite. Silicalite is uniquely suitable for the separation process of this invention for the presumed reason that its pores are of a size and shape that enable the silicalite to function as a molecular sieve, i.e. accept the molecules of fatty acids into its channels or internal structure, while rejecting the molecules of rosin acids. A detailed discussion of silicalite may be found in the article "Silicalite, A New Hydrophobic Crystalline Silica Molecular Sieve": *Nature*, Vol. 271, Feb. 9, 1978, incorporated herein by reference.

It is essential to the present invention that the silicalite be bound by silica, i.e. be in a silica matrix. The invention requires the incorporation of the silicalite into the silica by dispersing silicalite powder into a colloidal amorphous silica, to obtain a precursor, gelling the precursor, and then treating the gel in a manner effecting substantially complete elimination of hydroxyl groups on the silialite and silica matrix. The colloidal amorphous silica comprises an aqueous colloidal dispersion of amorphous silica particles and the gelation is preferably effected by removing water from the dispersion, although other means of gelling may be used, such as changing pH or adding a salt or water miscible organic solvent. The silicalite should be present in the silica matrix in amounts ranging from about 75 wt.% to about 98 wt.% silicalite based on volatile free composition. Prior to the treatment of the gel to eliminate hydroxyl groups it is preferably extruded while still in a plastic state and then broken into discrete particles. The plastic state will occur during at least a portion of the time water is being removed to achieve gelling. Following treatment, the particles may be further ground to a smaller size more physically suitable for use in the particular separation scheme employed, typically about 16–60 mesh (Standard U.S. Mesh).

The colloidal amorphous silica prefered for use in the present invention is that marketed by Du Pont Co. under the trademark "Ludox." Ludox colloidal silica is described as discrete uniform spheres of silica which have no internal surface area or detectable crystallinity dispersed in an alkaline medium which reacts with the silica surface to produce a negative charge. The pH of the alkaline medium is maintained from about 8.5 to about 11.0. The stabilizing cations in the alkaline medium may comprise sodium or ammonium ions. The concentration of silica in the colloidal dispersion may comprise from about 30 wt.% to about 50 wt.% based on $SiO_2$.

The Du Pont Co. literature describing Ludox colloidal silica states that during drying the hydroxyl groups on the surface of the silica particles condense by splitting out water to form siloxane bonds (Si—O—Si) resulting in coalescence, interbonding and particles which are chemically inert and heat-resistant. It was found, however, that mere drying of the silica-bound silicalite at conditions accepted in the art to be drying conditions, i.e. heating in air in an oven at a temperature slightly above 100° C., produces a molecular sieve unacceptable for use in separating the components of tall oil. Such a molecular sieve exhibits reactivity for the fatty and rosin acids and the separation achieved is very poor in that there are severe tailings of the rosin acid components into the fatty acid components. The reason hypothesized for such behavior is that the statements in the Du Pont Co. literature concerning the formation of siloxane bonds during conventional drying are substantially true, however, there is still a very minute amount of hydroxyl groups (or ammonium groups where the stabilizing cations are ammonium ions) left on the particles which for most practical purposes are of no consequence, but which render the adsorbent completely unsuitable for use in the process of the present invention. It should also be mentioned at this point that other binders for silicalite have been tried, but with equally poor results. Organic binders such as polyvinyl alcohol are unsuitable, probably because of the presence of hydroxyl groups. Natural clay binders exhibit selectivity for various constituents of tall oil and therefore interfere with the effect of the silicalite.

It is therefore necessary to treat the gelled silica-bound silicalite as aforesaid, to eliminate the hydroxyl groups and replace them by siloxane bonds. The resulting silicalite in a silica matrix molecular sieve obtained is uniquely suitable for separation of tall oil components since it achieves the excellent separation of pure silicalite and, at the same time, provides a physically strong and stable molecular sieve suitable for commercial separaration applications.

There are numerous ways of treating the gelled silica-bound silicate to achieve substantially complete elimination of hydroxyl groups. One way is thermal treatment at a temperature of from about 450° C. to about 1000° C. for a minimum time of from about 3 hours to about 48 hours which may occur in the presence of oxygen, nitrogen and/or hydrogen. Another way is by first contacting the molecular sieve with an alcohol, such as ethanol, and then thermally treating the molecular sieve at elevated temperature (in excess of about 350° C.) in the presence of oxygen. A third way of eliminating hydroxyl groups is by chlorination of the molecular sieve at elevated temperature, such as like taught in U.S. Pat. No. 4,308,172 to McDaniel whereby the molecular sieve is contacted at an elevated temperature with a chlorinating agent (e.g. $CCl_4$, $COCl_2$, $Cl_2$, $C_2Cl_4$, $SO_2Cl_2$ or $SOCl_2$), the resulting chlorinated molecular sieve is dechlorinated at an elevated temperature and the declorinated molecular sieve is oxidized at an elevated temperature. Another way to way to effect hydroxyl groups removal by chlorination is to contact the molecular sieve at an elevated temperature with a mixture containing oxygen and silicon tatrachloride.

The molecular sieve may be employed in the form of a dense compact fixed bed which is alternatively contacted with the feed mixture and displacement fluid. In the simplest embodiment of the invention, the molecular sieve is employed in the form of a single static bed in which case the process is only semi-continuous. In another embodiment, a set of two or more static beds may be employed in fixed bed contacting with appropriate valving so that the feed mixture is passed through one or more molecular sieve beds, while the displacement fluid can be passed through one or more of the other beds in the set. The flow of feed mixture and displacement fluid may be either up or down through the molecular sieve. Any of the conventional apparatus employed in static bed fluid-solid contacting may be used.

Countercurrent moving bed or simulated moving bed counter-current flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such a flow system are described in U.S. Pat. No. 2,985,589 incorporated herein by reference. In such a system, it is the progressive movement of multiple liquid access points down a molecular sieve chamber that simulates the upward movement of molecular sieve contained in the chamber. Only five of the access lines are active at any one time: the feed input stream, displacement fluid inlet stream, raffinate outlet stream, and extract outlet stream access lines. Coincident with this simulated upward movement of the solid molecular sieve is the movement of the liquid occupying the void volume of the packed bed of molecular sieve. So that countercurrent contact is maintained, a liquid flow down the molecular sieve chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the molecular sieve chamber into separate zones, each of which has a different function. In this embodiment of the process, it is generally necessary that three separate operational zones be present in order for the process to take place although in some instances an optional fourth zone may be used.

The retention zone, zone 1, is defined as the molecular sieve located between the feed inlet stream and the raffinate outlet stream. In this zone, the feedstock contacts the molecular sieve, an extract component is retained, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams. The liquid flush stream (diluent) may be introduced in zone 1 at a point slightly downstream of the feed inlet stream. The diluent, if used, will be added at a rate sufficient to displace the displacement fluid associated with at least the non-selective void volume of the packed bed of molecular sieve in simulated movement in zone 1, thereby facilitating the retention of the fatty acid.

Immediately upstream with respect to fluid flow in zone 1 is the purification zone, zone 2. The purification zone is defined as the molecular sieve between the extract outlet stream and the feed inlet stream. The basic operations taking place in zone 2 are the displacement from the non-selective void volume of the molecular sieve by a circulating stream of any raffinate material carried into zone 2 by the shifting of molecular sieve into this zone and the displacement of any raffinate material retained within the selective pore volume of the molecular sieve or retained on the surfaces of the molecular sieve particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the displacement zone, zone 3. The displacement zone is defined as the molecular sieve between the displacement fluid inlet and the extract outlet streams. The function of the displacement zone is to allow a displacement fluid which passes into this zone to displace the extract component which was retained in the molecular sieve during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the molecular sieve between the raffinate outlet stream and the displacement fluid inlet stream, if used, is located immediately upstream with respect to the fluid flow to zone 3. Zone 4 would be utilized to conserve the amount of displacement fluid utilized in the displacement step since a portion of the raffinate stream which is removed from zone 1 can be passed into zone 4 to displace displacement fluid present in that zone out of that zone into the displacement fluid zone. Zone 4 will contain enough molecular sieve so that raffinate material present in the raffinate stream passing out of zone 1 and into zone 4 can be prevented from passing into zone 3 thereby contaminating extract stream removed from zone 3. In the instances in which the fourth operational zone is not utilized, the raffinate stream which would have passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

In the most preferred embodiment of the present invention, zone 4 wil be employed and the liquid flush diluent stream, if used, may be introduced not into zone 1, but into zone 4 at the upstream boundary of zone 4. In this way, the displacement fluid that would otherwise move into zone 4 from zone 3 as part of the simulated moving bed will be kept in zone 3, assuming that the correct amount of liquid flush is used. This will also reduce the displacement fluid requirements. Thus, when the molecular sieve enters zone 1, it will have the proper minimum displacement fluid environment.

A cyclic advancement of the input and output streams through the fixed bed of molecular sieve can be accomplished by utilizing a manifold system in which the valves in the manifold are operated in a sequential manner to effect the shifting of the input and output streams thereby allowing a flow of fluid with respect to solid molecular sieve in a countercurrent manner. Another mode of operation which can effect the countercurrent flow of solid molecular sieve with respect to fluid involves the use of a rotating disc valve in which the input and output streams are connected to the valve and the lines through which feed input, extract output, displacement fluid input and raffinate output streams pass are advanced in the same direction through the molecular sieve bed. Both the manifold arrangement and disc valve are known in the art. Specifically, rotary disc vlves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of molecular sieve than some other operational zone. For instance, in some operations the buffer zone can contain a minor amount of molecular sieve as compared to the molecular sieve required for the retention and purification zones. It can also be seen that in instances in which displacement fluid is used which can easily displace extract material from the molecular sieve that a relatively small amount of molecular sieve will be needed in a displacement zone as compared to the molecular sieve needed in the buffer zone or retention zone or purification zone or all of them. Since it is not required that the molecular sieve be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the displacement fluid including diluent can be separated to produce an extract product containing a reduced concentration of displacement fluid. Preferably, but not necessary to the operation of the process, at least a portion of the raffinate output stream will also be passed to a separation means wherein at least a portion of the diluent can be separated to produce a diluent stream which can be reused in the process and a raffinate product containing a reduced concentration of diluent. The separation means will typically be a fractionation column, the design and operation of which is well known to the separation art.

Reference can be made to D. B. Broughton U.S. Pat. No. 2,985,589, and to a paper entitled "Continuous Adsorptive Processing—A New Separation Technique" by D. B. Broughton represented at the 34th Annul Meeting of the Society of Chemical Engineers at Tokyo, Japan on Apr. 2, 1969, both references incorporated herein by reference, for further explanation of the simulated moving bed countercurrent process flow scheme.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Separation conditions will include a temperature range of from about 20° to about 200° C. with about 20° to about 100° C. being more preferred and a pressure sufficient to maintain liquid phase. Displacement conditions will include the same range of temperatures and pressures as used for separation conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

A dynamic testing apparatus is employed to test various molecular sieves with a particular feed mixture and displacement fluid to measure the molecular sieve characteristics of retention capacity and exchange rate. The apparatus consists of a helical molecular sieve chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the molecular sieve chamber. A pulse test, performed using this apparatus and the following general procedure, is used to determine data for various molecular sieve systems. The molecular sieve is filled to equilibrium with a particular displacement fluid material by passing the displacement fluid through the molecular sieve chamber. At a convenient time, a pulse of feed containing known concentrations of a tracer and of a particular extract component or of a raffinate component or both, all diluted in displacement fluid is injected for a duration of several minutes. Displacement fluid flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, molecular sieve performance can be rated in terms of void volume, retention volume for an extract or a raffinate component, and the rate of displacement of an extract component from the molecular sieve. The retention volume of an extract or a raffinate component may be characterized by the distance between the center of the peak envelope of the tracer component or some other known reference point. It is expressed in terms of the volume in cubic centimeters of displacement fluid pumped during this time interval represented by the distance between the peak envelopes. The rate of exchange of an extract component with the displacement fluid can generally be characterized by the width of the peak envelopes at half intensity. The narrowerthe peak width, the faster the displacement rate. The displacement rate can also be characterized by the distance between the center of the tracer peak envelope and the disappearance of an extract component which has just been displaced. This distance is again the volume of displacement fluid pumped during this time interval.

The following non-limiting working example is presented to illustrate the process of the present invention and is not intended to unduly restrict the scope of the claims attached hereto.

EXAMPLE

The above described pulse test apparatus was used to obtain data for this example. The liquid temperature was 60° C. and the flow was up the column at the rate of 1.2 ml/min. The feed stream comprised 20 wt.% distilled tall oil, and 80 wt.% displacement fluid. The column was packed with 23 wt.% Ludox bound silicalite which had been prepared as required in the practice of the present invention, including gelation by removal of water (drying) followed by treatment for removal of hydroxyl groups, which in this case was by heating in air at 1000° C. for 48 hours. The resulting molecular sieve was then ground and screened to 20–50 mesh. The displacement fluid used was 80 LV % methylethylketone and 20 LV % acetic acid.

The results of this example are shown on the accompanying figure. It is immediately apparent from the figure that the separation capable of being achieved by the present invention is excellent. The separation of the rosin acid from fatty acid curves is clear and distinct. Effective and practical separation of tall oil components has thus become a reality.

Additional runs on the pulse test apparatus were carried out, also in accordance with the present invention, but with different displacement fluids such as a propionic acid and heptane mixture and pentanoic acid. The results varied somewhat as to the quality of separation, but in all cases clear separations were achieved. The combination of organic acid and diluent as set forth in this example appears to be among the most effective.

The curves also illustrate that there is not a trace of the aforementioned reactivity between adsorbent and feed components or tailings of rosin acid components into the fatty acid components previously observed to occur with the silicalite with an organic binder and silicalite with a silica binder not thermally treated in accordance with the present invention.

What is claimed is:

1. A process for separating a fatty acid from a mixture comprising a fatty acid and a rosin acid, said process comprising contacting said mixture at separation conditions with a molecular sieve comprising silicalite in a silica matrix the precursor of said molecular sieve comprising silicalite powder dispersed in colloidal amorphous silica, said precursor having been gelled and then treated in a manner effecting substantially complete elimination of hydroxyl groups on said molecular sieve, to provide that said molecular sieve selectively retains said fatty acid thereon to the exclusion of said rosin acid which is removed from the fatty acid containing molecular sieve.

2. The process of claim 1 wherein said fatty acid is recovered from said molecular sieve by displacement with a displacement fluid at displacement conditions.

3. The process of claim 2 wherein said displacement fluid comprises an organic acid.

4. The process of claim 2 wherein said process is cyclical and said molecular sieve is flushed with a diluent at flushing conditions prior to each contacting of said feed mixture with said molecular sieve.

5. The process of claim 4 wherein said separation, flushing and displacement conditions include a temperature within the range of from about 20° C. to about 200° C. and a pressure sufficient to maintain liquid phase.

6. The process of claim 3 wherein said displacement fluid comprises a solution of organic acid and diluent, said diluent being soluble in said feed mixture and having a polarity index of at least 3.5.

7. The process of claim 6 wherein said organic acid comprises a compound having from 2 to 5 carbon atoms per molecule and said diluent comprises methylethylketone or acetone.

8. The process of claim 3 wherein said separation and displacement conditions include a temperature within the range of from about 20° C. to about 200° C. and a pressure sufficient to maintain liquid phase.

9. The process of claim 1 wherein said precursor comprises an aqueous colloidal dispersion of amorphous silica particles and silicalite powder and said gelation is effected by removing water from said dispersion.

10. The process of claim 1 wherein said precursor is extruded and broken into discrete particles prior to said elimination of hydroxyl groups.

11. A process for separating a fatty acid from a mixture comprising a fatty acid and a rosin acid, which process employs a molecular sieve comprising silicalite in a silica matrix, the precursor of said molecular sieve comprising silicalite powder dispersed in colloidal amorphous silica, said precursor having been gelled and then treated in a manner effecting substantially complete elimination of hydroxyl groups on said molecular sieve, which process comprises the steps of:

(a) maintaining net liquid flow through a column of said molecular sieve in a single direction, which column contains at least three zones having separate operational functions occurring therein and being serially interconnected with the terminal zones of said column connected to provide a continuous connection of said zones;

(b) maintaining a retention zone in said column, said zone defined by the molecular sieve located between a feed inlet stream at an upstream boundary of said zone and a raffinate outlet stream at a downstream boundary of said zone;

(c) maintaining a purification zone immediately upstream from said retention zone, said purification zone defined by the molecular sieve located between an extract outlet stream at an upstream boundary of said purification zone and said feed inlet stream at a downstream boundary of said purification zone;

(d) maintaining a displacement zone immediately upstream from said purification zone, said displacement zone defined by the molecular sieve located between a displacement fluid inlet stream at an upstream boundary of said zone and said extract outlet stream at a downstream boundary of said zone;

(e) passing said feed stream into said retention zone at separation conditions to effect the selective retention of said fatty acid by said molecular sieve in said retention zone and withdrawing a raffinate outlet stream from said retention zone comprising said rosin acid;

(f) passing a displacement fluid into said displacement zone at displacement conditions to effect the displacement of said fatty acid from the adsorbent in said displacement zone;

(g) withdrawing an extract stream comprising said fatty acid and displacement fluid from said displacement zone;

(h) periodically advancing through said column of molecular sieve in a downstream direction with respect to fluid flow in said retention zone the feed inlet stream, raffinate outlet stream, displacement fluid inlet stream, and extract outlet and raffinate outlet streams.

12. The process of claim 11 wherein said displacement fluid comprises an organic acid.

13. The process of claim 12 wherein a diluent inlet stream is passed into said retention zone downstream of said feed inlet stream to effect the flushing of said molecular sieve in said retention zone, said diluent inlet stream being advanced with the other process streams as in step (h).

14. The process of claim 13 wherein said separation, flushing and displacement conditions include a temperature within the range of from about 20° C. to about 200° C. and a pressure sufficient to maintain liquid phase.

15. The process of claim 12 wherein said displacement fluid comprises a solution of organic acid and diluent, said diluent being soluble in said feed mixture and having a polarity index of at least 3.5.

16. The process of claim 15 wherein said organic acid comprises a compound having from 2 to 5 carbon atoms per molecule and said diluent comprises methylethylketone or acetone.

17. The process of claim 11 further characterized in that it includes the step of maintaining a buffer zone immediately upstream from said displacement zone, said buffer zone defined as the molecular sieve located between the displacement fluid input stream at a downstream boundary of said buffer zone and a raffinate output stream at an upstream boundary of said buffer zone.

18. The process of claim 17 wherein said displacement fluid comprises an organic acid.

19. The process of claim 18 wherein a diluent inlet stream is passed into said buffer zone at the upstream boundary of said zone to effect the flushing of molecular sieve in said buffer zone, said diluent inlet stream being advanced with the other process streams as in step (h).

20. The process of claim 11 wherein said precursor comprises an aqueous colloidal dispersion of amorphous silica particles and silicalite powder and said gelation is effected by removing water from said dispersion.

21. The process of claim 11 wherein said precursor is extruded and broken into discrete particles prior to said elimination of hydroxyl groups.

* * * * *